United States Patent
Michel et al.

(10) Patent No.: US 6,194,595 B1
(45) Date of Patent: Feb. 27, 2001

(54) PROCESS FOR THE PREPARATION OF MIXTURES OF ORGANOSILICON OLIGOSULFANES CONTAINING A HIGH PROPORTION OF ORGANOSILICON DISULFANES

(75) Inventors: Rudolf Michel, Freigericht; Jörg Münzenberg, Hanau, both of (DE)

(73) Assignee: Degussa-Hüls Aktiengesellschaft, Frankfurt (DE)

( * ) Notice: Subject to any disclaimer, the term of this patent is extended or adjusted under 35 U.S.C. 154(b) by 0 days.

(21) Appl. No.: 09/299,627

(22) Filed: Apr. 27, 1999

(30) Foreign Application Priority Data

Apr. 30, 1998 (DE) ................................ 198 19 373

(51) Int. Cl.$^7$ ...................................................... C07F 7/08
(52) U.S. Cl. ............................................................ 556/427
(58) Field of Search .............................................. 556/427

(56) References Cited

U.S. PATENT DOCUMENTS

| | | |
|---|---|---|
| 3,842,111 | 10/1974 | Meyer-Simon et al. . |
| 3,978,103 | 8/1976 | Meyer-Simon et al. . |
| 4,129,585 | 12/1978 | Buder et al. . |
| 4,507,490 * | 3/1985 | Panster et al. ........................ 556/427 |
| 4,595,740 * | 6/1986 | Panster .................................... 528/30 |
| 5,440,064 * | 8/1995 | Agostini et al. ...................... 556/427 |
| 5,466,848 | 11/1995 | Childress . |
| 5,468,893 * | 11/1995 | Parker et al. .......................... 556/427 |
| 5,489,701 | 2/1996 | Childress et al. . |
| 5,580,919 | 12/1996 | Agostini et al. . |
| 5,583,245 * | 12/1996 | Parker et al. .......................... 556/427 |
| 5,663,395 * | 9/1997 | Gobel et al. ........................... 556/427 |
| 5,859,275 * | 1/1999 | Munzenberg et al. ............... 556/427 |
| 5,892,085 * | 4/1999 | Munzenberg et al. ............... 556/427 |

FOREIGN PATENT DOCUMENTS 0326914  8/1989  (EP) .

OTHER PUBLICATIONS

Database WPI on Questel, Woche 9543, London: Derwent Publications Ltd., AN 95–332519 & JP 07228588.

* cited by examiner

*Primary Examiner*—Paul F. Shaver
(74) *Attorney, Agent, or Firm*—Smith, Gambrell & Russell, LLP

(57) ABSTRACT

A process for the preparation of mixtures of organosilicon disulfanes with a high disulfane content includes first reacting finely divided sodium and sulfur in an organic solvent, and then reacting the resulting $Na_2S_x$ product further with a halogenoalkylalkoxysilane to give the desired product.

8 Claims, No Drawings

PROCESS FOR THE PREPARATION OF MIXTURES OF ORGANOSILICON OLIGOSULFANES CONTAINING A HIGH PROPORTION OF ORGANOSILICON DISULFANES

FIELD OF THE INVENTION

The invention relates to the preparation of organosilicon oligosulfane mixtures containing a high proportion of disulfanes.

BACKGROUND OF THE INVENTION

Processes for the preparation of oligosulfanes have long been known. Various known systems are described below.

DE-PS 2141159 (U.S. Pat. No. 3,842,111) describes a process for the preparation of bis-(alkoxysilylalkyl) oligosulfanes from the corresponding halogen alkylalkoxysilane and alkali metal oligosulfides, preferably in alcoholic solution. However, only mixtures of sulfanes with different chain lengths are produced. These patent documents are entirely incorporated herein by reference.

In a process described in DE-PS 2712866 (U.S. Pat. No. 4,129,585), an alkali metal alcoholate is reacted with a halogen alkylalkoxysilane, metal or ammonium hydrogen sulfide, and sulfur in the presence of an organic solvent. However, the preparation of the alkali metal alcoholate solution is very time-consuming, which makes industrial-scale use of this process problematic. These patent documents also are entirely incorporated herein by reference.

U.S. Pat. No. 5,466,848 discloses a process in which hydrogen sulfide is reacted with an alkoxide, and the reaction product is treated with elemental sulfur, and then with a halogen alkylalkoxysilane, to give the desired organosilicon polysulfane. Likewise, the process according to U.S. Pat. No. 5,489,701 involves working with alkoxides and hydrogen sulfide, a compound which is known to be very unpleasant to handle. JP-OS 7-228588 describes the reaction of anhydrous sodium sulfide and sulfur with halogen alkoxysilanes. This procedure gives a mixture of polysulfanes, as experiments have shown. These three patent documents also are entirely incorporated herein by reference.

Organosilicon polysulfanes, and especially bis(triethoxysilylpropyl)tetrasulfane, are used in combination with highly active silicic acid fillers in the manufacture of vulcanized rubber articles, especially tires.

The advantageous use of high purity disulfanes in terms of both the processing of the material, and of the resulting properties of the vulcanizates, is set out in EP-A 0 732 362 (U.S. Pat. No. 5,580,919) and by Panzer (L. Panzer, American Chem. Soc., Rubber Div. Meeting, 1997). These documents also are entirely incorporated herein by reference.

The $Na_2S_x$ required for disulfane preparation can be obtained by reacting sulfur and sodium in molten form, as described in DE-PS 38 03 243, which document is entirely incorporated herein by reference. It should be noted, however, that the melting point of the polysulfide is inversely proportional to its sulfur content. Thus, for example, the $Na_2S_2$ required to produce oligosulfane mixtures of high disulfane content has a melting point of 474° C. The only suitable reactor material for such a high temperature is graphite. The difficulties of obtaining reactor components in the necessary dimensions makes industrial application of this process impractical.

DESCRIPTION OF THE INVENTION

The object of the invention is to provide a process for the preparation of organosilicon disulfanes, which process uses a $Na_2S_x$ product prepared from elemental sodium and sulfur.

The invention provides a process for the preparation of organosilicon disulfanes of the general formula:

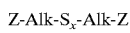  (1)

in which the Z components, which may be the same or different, represent the groupings:

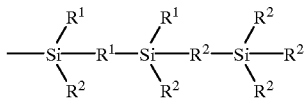

in which each $R^1$ in the formula, which may be the same as or different from the other $R^1$ groups in the formula, is a linear or branched alkyl group having 1–6 carbon atoms, a cycloalkyl radical having 5–8 carbon atoms, a benzyl radical, or a phenyl radical optionally substituted by methyl, ethyl or chlorine, and wherein each $R^2$ in the formula, which may be the same as or different from the other $R^2$ groups in the fonnula, is an alkoxy group with a linear or branched carbon chain having 1–6 carbon atoms, a cycloalkoxy group having 5–8 carbon atoms, a phenoxy group, or a benzyloxy group, and wherein Alk, each of which may be the same or different, is preferably a divalent, saturated linear or branched hydrocarbon radical having 1–10 carbon atoms, preferably methylene, as well as preferably ethylene, i-propylene, n-propylene, i-butylene or n-butylene, also n-pentylene, 2-methylbutylene, 3-methylbutylcne, n-pentylene, 1,3-dimethylpropylene and 2,3-dimethylpropylene, with n-propylene being particularly suitable, or the group

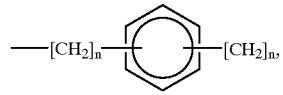

where n=1–4 (wherein each "n" may be the same or different), and wherein x=1.5 to 3.0.

The process includes a two-step reaction, in which:
1. suspensions of finely divided sodium are reacted with sulfur in amounts corresponding to the stoichiometry of the $Na_2S_x$ product to be produced (e.g., in approximately equimolar amounts for a disulfane product), in an inert organic solvent at temperatures above 98° C., and optionally washed and dried (to thereby form an $Na_2S_x$ product), and then
2. the $Na_2S_x$ product is partially or completely dissolved or suspended in an inert organic solvent, and this solution or suspension is reacted with an organosilicon compound of general formula (II):

  (II), in which Z and Alk are as defined above and Hal is a chlorine or bromine atom. After this second reaction step, the desired oligosulfane mixture is isolated.

The proportion of disulfane is preferably 55 to 100 wt. %, and more preferably 55 to 75 wt. %.

The desired oligosulfane mixture may be isolated by any suitable procedure known in the art. For example, the precipitate of inorganic halide can be filtered off, and the solvent can be separated off by distillation or evaporation.

Suitable solvents for step 1 are the known aliphatic hydrocarbons with a carbon chain length of 7 to 12 carbon atoms, and especially 7 to 9 carbon atoms; aromatic hydrocarbons, such as toluene, xylene, ethylbenzene, mesitylene, naphthalene, and tetrahydronaphthalene; or high-boiling ethers, such as ethylene glycol diethyl ether, dibutyl ether, dipentyl ether, and anisole; or mixtures of these solvents. Common features of these solvents are that they preferably boil above 98° C. and at least partially dissolve sulfur.

Advantageously, the sodium is present in the form of small molten beads, so that no passivation of the surfaces occurs due to the reactions with sulfur.

It is possible, however, to use solvents with a lower boiling point if the reaction is carried out under a pressure elevated above atmospheric pressure. The latter variant (i.e., using elevated pressure) is naturally also applicable to use with higher-boiling compounds.

In a preferred embodiment, a suspension of finely divided sodium, in the same solvent as the suspension of sulfur, is added dropwise to the latter.

However, it is also possible to meter finely divided sulfur into a sodium dispersion. In any case, it must be noted that the reaction of these elements is strongly exothermic, although this reaction is readily controllable by those skilled in the art.

The reaction takes place at temperatures of greater than 98° C. to 250° C., and preferably at 100 to 150° C.

Another advantageous embodiment of the invention includes a process wherein sodium and sulfur in the form of suspensions in the same solvents are introduced simultaneously into a cylindrical reactor at spatially separated points, the sulfur being added outside the sodium/sulfur reaction zone and in the agitated flow, as far as possible upstream of the sodium addition point.

The starting substances of formula (II) for the second step of the process can be prepared by the skilled artisan through known processes and are generally available.

Organic solvents which can be used for the second reaction step of the process according to the invention are basically any polar substances in which the $Na_2S_x$ is at least partially soluble and which do not react with the organo-silicon compound of formula (II). A linear or branched alcohol having 1–5 carbon atoms, e.g., methyl, ethyl, propyl, butyl or pentyl alcohol, is preferably used as this organic solvent. Cycloalkyl alcohols having 5 to 8 carbon atoms, phenol, or benzyl alcohol are also suitable.

It is advantageous to use the alcohol corresponding to the particular $R^2$ group, for example, to avoid a transesterification. It is also advantageous, if appropriate, to use a mixture of these alcohols, for example, if $R^2$ in a compound of formula (I) has different meanings.

The process according to the invention affords a very pure disulfane with an average sulfur chain length of 1.97 to 2.06, which, in respect of the disulfide content, is markedly superior to the products prepared according to the state of the art, without a further purification step.

The following examples are provided to more clearly describe specific embodiments of the invention. These examples should be construed as illustrating this invention, and not as limiting it.

EXAMPLE 1

In a 500 ml three-necked flask equipped with a reflux condenser, a stirred dropping funnel, and a stirrer, a suspension of 11.5 g (0.50 mol) of finely divided sodium in 100 ml of xylene was added dropwise at 140° C., with stirring, to a suspension of 16.8 g (0.52 mol) of sulfur in 100 ml of xylene. The reaction is strongly exothermic. When the exothermicity has subsided after the drop-wise addition, a greyish-yellow heterogeneous reaction mixture is obtained which is kept at 140° C. for a further 30 minutes. After cooling, the solid is filtered off and rinsed with a low-boiling petroleum ether. The filter cake is dried by having dry nitrogen blown through it.

The dried filter cake is placed in 220 ml of ethanol in a 500 ml three-necked flask equipped with a stirrer, a dropping funnel, and a reflux condenser. A yellow solution is formed which warms to 65° C. After heating to 80° C., 114.4 g (0.48 mol) of 3-chloropropyltri-ethoxysilane are added dropwise to the boiling solution. When the dropwise addition has ended, the reaction mixture is left to react for a further 2.5 hours, with stirring, and cooled, and the insoluble material filtered off. The filter cake is rinsed four times with 50 ml of ethanol, and the filtrates are combined with the bulk solution. After evaporation under vacuum at 120° C. with a final vacuum of 40 mbar, 109.9 g of a brown liquid are obtained which, according to its $_1$H NMR spectrum, includes an oligosulfane mixture of the general fonnula [(EtO)$_3$SiCH$_2$CH$_2$CH$_2$]$_2$S$_x$ with an average sulfur chain length of 2.06. The yield is 92%, based on the amount of sodium used.

EXAMPLE 2

11.5 g (0.5 mol) of sodium is placed in 100 ml of xylene in a 250 ml three-necked flask equipped with a reflux condenser, a solid metering device, an Ultra-Turrax, and a stirrter. After heating to 110°C., the sodium is finely dispersed with the Ultra-Turrax. 16.0 g (0.5 mol) of sulfur is then added via the solid metering device, a violent reaction with fire occurring immediately on contact with the sodium suspension. While the sulfur is being metered in, the Ultra-Turrax is run 12 times for 1 minute in order to redisperse the sodium. When the metered addition has ended, the mixture was left to stand for a further 1 hour at 140–142° C., with stirring. After cooling, the yellow solid formed was filtered off and dried by having dry nitrogen blown through it.

The dried filter cake is placed in 220 ml of ethanol in a 500 ml three-necked flask equipped with a stirrer, a dropping funnel, and a reflux condenser. A yellow solution is formed which warms to 40° C. After heating to 80° C., 120.4 g (0.50 mol) of 3 3-chloropropyltri-ethoxysilane is added drop-wise to the boiling solution. When the drop-wise addition has ended, the reaction mixture is left to rcact for a further 2 hours, with stirring, and cooled, and the insoluble material is filtered off. The filter cake is rinsed four times with 50 ml of ethanol and the filtrates are combined with the bulk solution. After evaporation under vacuum at 120° C. with a final vacuum of 40 mbar, 110.6 g of a brown liquid is obtained which, according to its $_1$H NMR spectrum, includes an oligosulfane mixture of the general formula [(EtO)$_3$SiCH$_2$CH$_2$CH$_2$]$_2$S$_x$ with an average sulfur chain length of 1.97. The yield is 93%, based on the amount of sodium used.

Further modifications and variations of the foregoing will be apparent to those skilled in the art, and are intended to be encompassed by the claims appended hereto.

German priority application 198 19 373.4 is relied upon and incorporated herein by reference in its entirety.

We claim:

1. A process for preparing a mixture of organosilicon oligosulfanes containing a high proportion of disulfanes of the general formula:

Z-Alk-S$_x$-Alk-Z  (I)

wherein each Z, which may be the same or different, represents the group:

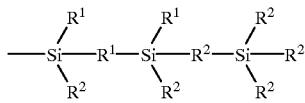

wherein each R¹, which may be the same or different, is a member selected from the group consisting of a linear or branched alkyl group having 1–6 carbon atoms, a cycloalkyl radical having 5–8 carbon atoms, a benzyl radical, and a phenyl radical, wherein said phenyl radical may be optionally substituted by methyl, ethyl or chlorine; and wherein each R², which may be the same or different, is a member selected from the group consisting of an alkoxy group with a linear or branched carbon chain having 1–6 carbon atoms, a cycloalkoxy group having 5–8 carbon atoms, a phenoxy group, and a benzyloxy group, wherein each Alk, which may be the same or different, is a divalent, saturated linear or branched hydrocarbon radical having 1–10 carbon atoms, or the group

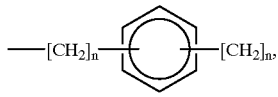

wherein each n, which may be the same or different, is from 1 to 4, and wherein x is from 1.5 to 3.0, the process comprising:

reacting a suspension of finely divided sodium with sulfur, in amounts corresponding to a stoichiometry of an $Na_2S_x$ product to be prepared, in a first inert organic solvent, at temperatures above 98° C., under an inert gas, to thereby form the $Na_2S_x$ product;

filtering the $Na_2S_x$ product;

dissolving or suspending the $Na_2S_x$ product, partially or completely, in a second inert organic solvent;

reacting the $Na_2S_x$ in the second organic solvent with a compound of general formula (II):

Z-Alk-Hal (II), wherein Z and Alk are as defined above, and wherein Hal is a chlorine or bromine atom, to thereby form an organosulfane mixture; and isolating the organosulfane mixture.

2. The process according to claim 1, wherein the first inert organic solvent has a boiling point greater than 98° C., and at least partially dissolves sulfur.

3. The process according to claim 1, wherein the reacting of finely divided sodium with sulfur is carried out under a pressure greater than atmospheric pressure.

4. The process according to claim 2, wherein the reacting of finely divided sodium with sulfur is carried out under a pressure greater than atmospheric pressure.

5. The process according to claim 1, wherein the sodium and the sulfur to be reacted in suspension are introduced simultaneously into a cylindrical reactor at spatially separated points.

6. The process according to claim 2, wherein the sodium and the sulfur to be reacted in suspension are introduced simultaneously into a cylindrical reactor at spatially separated points.

7. The process according to claim 3, wherein the sodium and the sulfur to be reacted in suspension are introduced simultaneously into a cylindrical reactor at spatially separated points.

8. The process according to claim 4, wherein the sodium and the sulfur to be reacted in suspension are introduced simultaneously into a cylindrical reactor at spatially separated points.

* * * * *